United States Patent [19]

Greyson et al.

[11] 4,015,462
[45] Apr. 5, 1977

[54] DEVICE AND METHOD FOR THE DETERMINATION OF THE SPECIFIC GRAVITY OR OSMOLALITY OF A LIQUID

[75] Inventors: Jerome Greyson; Sisto Nicholas Stiso, both of Elkhart, Ind.

[73] Assignee: Miles Laboratories, Inc., Elkhart, Ind.

[22] Filed: Jan. 8, 1976

[21] Appl. No.: 647,416

[52] U.S. Cl. .............................. 73/32 R; 23/230 B; 23/253 TP; 73/64.3
[51] Int. Cl.² ................... G01N 9/00; G01N 13/04
[58] Field of Search ..................... 73/32 R, 64.3; 116/114 AM; 23/230 B, 253 TP

[56] References Cited

UNITED STATES PATENTS 3,092,463  6/1963  Adams, Jr. et al. ........... 23/253 TP
3,932,132  1/1976  Hijikata ..................... 23/253 TP X

*Primary Examiner*—Richard C. Queisser
*Assistant Examiner*—Joseph W. Roskos
*Attorney, Agent, or Firm*—Richard W. Winchell

[57] ABSTRACT

Devices and methods are provided for determining specific gravity or osmolality of liquids. The preferred devices comprise a carrier matrix incorporated with microcapsules having osmotically fragile, semipermeable polymeric membrane walls encapsulating therein a solute and a coloring substance. In use, the test device is contacted with the liquid to be tested, and color change on the carrier matrix is observed as a measure of the specific gravity or osmolality of the liquid.

7 Claims, No Drawings

DEVICE AND METHOD FOR THE DETERMINATION OF THE SPECIFIC GRAVITY OR OSMOLALITY OF A LIQUID

BACKGROUND OF THE INVENTION

The determination of specific gravity or osmolality of liquids has long been recognized as a useful aid in the determination of solute concentration. In the clinical laboratory, the specific gravity or osmolality of body fluids, particularly urine, is a valuable aid in the diagnosis of many abnormal conditions such as kidney failure.

Various procedures and devices are described in the literature for the determination of specific gravity. For example, routine specific gravity determinations are made with hydrometers, pycnometers, gravitometers, urinometers, and the like. Although these prior art procedures are highly sensitive, they all require bulky instruments or devices which must be consistently cleaned, maintained and adjusted to produce reliable results. In addition, the prior art methods and devices require a relatively large sample volume and are time consuming. Therefore, it is considered highly desirable to provide a sensitive, rapid and reliable procedure and device for the determination of specific gravity or osmolality.

SUMMARY OF THE INVENTION

In accordance with the present invention, novel devices and methods are provided for the determination of specific gravity or osmolality of liquids. The preferred devices comprise a carrier matrix incorporated with microcapsules having osmotically fragile, semipermeable, polymeric membrane walls encapsulating therein a solute and a coloring substance, wherein said capsules are capable of releasing their encapsulated contents based upon a preselected initial osmotic gradient across the capsule wall.

DESCRIPTION OF THE INVENTION

The microcapsules found to be satisfactory for use in present invention have an osmotically fragile, semipermeable polymeric membrane wall capable of encapsulating therein an internal phase containing a solute and a suitable coloring substance, such as a dye or dye precursor. A suitable solute is provided in sufficient quantity to define a desired internal specific gravity or osmolality. The term "osmotically fragile" refers to the ability of the capsule wall to react to internal hydrostatic pressure by rupturing or by otherwise changing the wall's physical characteristics to allow the release of the internal phase. The term "semipermeable" refers to the ability of the membrane wall to be permeable to the solvent portion of the external liquid to be tested and to be impermeable to the solute portion of the internal phase. Specific gravity of a liquid is defined as the ratio of the density of the liquid to that of a standard liquid, e.g., water. In the context of this disclosure the liquid whose specific gravity or osmolality is to be determined, shall be defined as a pure solvent or as a mixture of substances in solution whose aggregate is in a homogenous liquid state. Osmolality is defined as the number of osmols of a solute per kilogram of a solvent. An osmol is a unit of osmotic pressure based upon the concentration of solute particles in solution.

In use, the microcapsules of this invention are contacted with a liquid to be tested having an unknown specific gravity or osmolality which is lower than that of the capsule's solute-containing internal phase. The solvent portion of said liquid, being permeable to the capsule wall, enters the capsule as a result of the osmotic driving force. Because of the osmotic gradient across the capsule wall thus produced, which gradient is, defined by the specific gravity or osmolality of the liquids internal and external thereto, sufficient pressure is developed within the capsule to cause swelling and/or rupture of the capsule wall and release of the contents of the capsule. The rate and extent of release of the capsule contents is a function of the initial osmotic gradient across the capsule wall and hence of the osmolality or specific gravity of the liquid external to the capsule.

Microcapsules useful in the present invention can be prepared by a variety of well known methods as described in Agnew. Chem. Internat. Edit., 14:539 (1975) and the references cited therein. Such methods include chemical encapsulation techniques such as interfacial polycondensation, coacervation, and the like; and physiomechanical techniques such as centrifugation, spray drying, and the like. Interfacial polycondensation techniques are preferred for ease of preparation of the microcapsules.

Using the interfacial polycondensation techniques, two reactive monomers or oligomers are brought together at a reaction interface where polycondensation can occur to form a thin polymeric film which is insoluble in the parent media of the reactants. Suitable microcapsules have been prepared by dissolving a first monomer component, such as a polyfunctional amine, in an aqueous phase containing a solute and a dye or dye precursor, and forming a dispersion or emulsion of the aqueous phase in a water immiscible reaction phase such as mineral oil. To this dispersed mixture is added a second monomer component, such as an acyl chloride, dissolved in an organic solvent miscible with the reaction phase. The result is the formation of a polymeric film, such as polyamide, insoluble in either phase, at the interface between the mutually immiscible phases. The aqueous phase, containing the solute and dye or dye precursor is thus encapsulated by the polymeric film as an internal phase.

Suitable polymeric materials useful to form the osmotically fragile semipermeable membrane wall of the microcapsules of the present invention include in addition to polyamide, polyester, polyurethane, polyurea and the like.

The physical and mechanical properties of the capsules that define the osmotic fragility and permeability of the capsule wall can be widely varied depending upon the specific gravity or osmolality and the type of liquid to be tested. It is known to use polymer crosslinking agents to increase impermeability, retentivity, and mechanical strength of the polymers. Surface active agents such as detergents can be added to decrease the size of the capsules. The monomer reaction times can be extended to increase the thickness of the capsule wall. Other well known methods such as control of reaction conditions, of polymer selection, of solvent selection and the like can also be used to vary the osmotic fragility and/or permeability of the capsule wall to suit the particular applications of the invention.

It has been found that the storage stability of microcapsules which contain an internal liquid phase can be surprisingly improved by desiccating the microcapsules. The capsules can be desiccated by such convenient means as vacuum drying, vacuum desiccant drying, freeze drying, critical point drying and the like. For example, polyamide microcapsules containing an internal aqueous phase of solute and dye or dye precursor can be desiccated in about 2 to 30 hours under reduced pressure, eg. at $10^{-1}$ to $10^{-4}$ Torr. By these means, the desiccated microcapsules have been shown to be stable for extended periods under forced storage stability conditions.

Suitable solutes, for use in the microcapsules to define the osmolality of the internal phase, are soluble in the liquid to be tested. Such solutes include most solvent soluble substances such as inorganic salts, organic salts, sugars and the like. For example, if the liquid to be tested is aqueous, then any suitable water soluble salt such as sodium chloride may be used. The concentration of the solute can be widely varied to impart to the inner phase a specific gravity or osmolality which is sufficiently greater than that of the liquid to be tested so that on contact of the microcapsules with said liquid the desired initial osmotic gradient across the capsule wall is established.

Suitable coloring substances are encapsulated in the microcapsules to provide an observable measure of the rate and extent of the content's release from the capsules. Examples of such coloring substances are the dyes: alizarin; bromothymol blue; crystal violet; Evans blue dye; malachite green; methyl orange; Prussian blue and the like. Dye precursors are substances which are normally colorless, but can react with one or more complementary substances to produce a dye, and hence a color. For example, diazonium salts couple with aromatic amines or phenols to produce highly colored azo compounds. Colors can also be generated from dye precursors through oxidation, reduction, pH change and other like means. Where a dye precursor is contained within the capsule, color is produced in combination with an externally located complementary dye component. A combination of microcapsules of varying mechanical and physical properties and containing different colored dyes or dye precursors can be prepared to provide a mixture of colors.

In a preferred embodiment of this invention, the above described microcapsules are incorporated on or with a carrier matrix and utilized as a dip-and-read type test device. The device may be prepared by various well known methods which include impregnating an absorbent matrix with the microcapsules described above, thus incorporating with and on the matrix a finely divided intimate mixture of the microcapsules. Binders may be useful to adhere the microcapsules to the matrix. Suitable absorbent matrices which may be used include paper, cellulose, wood, synthetic resin fleeces, glass fiber paper, polypropylene felt, nonwoven and woven fabrics and the like. Suitable binders which may be used are immiscible with the test sample but allow the test sample to be absorbed into the matrix. Such binders include cellulose acetate, cellulose acetate butyrate, hydroxy propyl cellulose, carboxy methyl cellulose, polyvinylpyrrolidone, gelatin, gum arabic and the like. The impregnated matrix so prepared is advantageously affixed by suitable means to a carrier member, such as an organoplastic strip, for ease of use.

Where the microcapsules contain a dye precursor, one or more complementary dye components can be incorporated with the matrix. Such complementary dye components include, for example, diazonium salts, aromatic amines, phenols, oxidizing agents, reducing agents, pH modifiers and the like.

In use of the test device, the impregnated matrix portion thereof is immersed in the liquid to be tested and is immediately withdrawn. If the liquid thus contacted has a lower osmolality or specific gravity than that of the internal phase of the microcapsules, the solvent portion of said liquid enters the capsules, and the contents thereof are released by the resulting increased internal pressure. The contents thus color the matrix. The color which results is then compared with precalibrated color standards to determine the specific gravity or osmolality of the liquid tested. Precalibrated color standards are prepared using test liquids of known specific gravity and microcapsules prepared in the same manner as those in the test device used. In addition to visual comparison, various instrumental methods may also be employed to determine the quality of the color developed, thus increasing the accuracy of the test by obviating the subjective determination of color by the human eye.

It has been found that the devices of this invention are highly sensitive. The devices prepared as described herein are capable of resolving 0.010 specific gravity units in the specific gravity range of about 1.000 to 1.050. Such devices are particularly useful in determining the specific gravity of such liquids as saline solutions and such biological liquids as urine. However, it will be obvious to one skilled in the art that test devices of the present inventions which are useful in determining the specific gravity of liquids within other specific gravity ranges can be prepared by the use of microcapsules having suitable osmotic fragility and permeability and an internal phase of suitable specific gravity or osmolality.

The following illustrative examples are provided to further describe the inventions but are not intended to limit the scope of the invention.

EXAMPLE 1

This example illustrates a typical method for preparing microcapsules and a method for using the microcapsules to determine specific gravity or osmolality.

In this instance, an aqueous solution of sodium chloride and Evans blue dye were encapsulated within a polyamide membrane. The following charges were prepared:

| In flask: | 55 ml mineral oil |
| --- | --- |
| | 25 ml carbon tetrachloride |
| | 1 gm bentonite |
| | 3 µl Sorbitan Trioleate (Span 85) |
| In 1st beaker: | 3 ml 1M NaCl |
| | 0.4 gm NaOH |
| | 0.75 ml ethylenediamine |
| | 0.75 ml diethylendiamine |
| | 0.5 gm Evans blue dye |
| In 2nd beaker: | 6 ml carbon tetrachloride |
| | 6 ml pentane |
| | 3 ml sebacyl chloride |

The aqueous amine-containing solution of the 1st beaker was added to and dispersed in the reaction medium contained in the flask using a magnetic stirrer at its highest speed for about 20 seconds. The stirring rate was then reduced to a speed just sufficient to keep the dispersion from settling. The organic solution of polyfunctional acyl chloride contained in the 2nd beaker was then rapidly added to the dispersion in the flask, and the resulting reaction produced the afore described capsules having the aqueous phase encapsulated therein. Stirring was continued for about 1 hour. The capsules were separated from the reaction media by filtration and washed with petroleum ether and air dried. About 20% of the capsules were 500μ or larger in diameter, 60% were 250 to 500μ in diameter and 20% were smaller than 250μ in diameter.

The following procedure was followed to determine the rate and extent of release of the internal phase from the capsules under test conditions. About 25 mg of the above prepared dry microcapsules were placed into each of five standard spectrophotometric cuvettes. Five aqueous solutions containing various concentrations of NaCl between 0 and 4 M, corresponding to a specific gravity range of between 1.000 and 1.100, were used as test solutions. About 3 ml of a test solution was added to each cuvette containing the microcapsules, and 15 seconds after the addition of the test solution, each cuvette and its contents were agitated briefly and placed in a Beckman DK-2a spectrophotomer. At 30 sec intervals thereafter, the absorbance of each test solution was measured at 575 nm, the wavelength of maximum absorption for Evans Blue dye in the visible spectral region. Measurements were made at the specified 30 sec intervals for 6 minutes. The amount of dye released from the capsules, as evidenced by the intensity of the blue color produced in the test solutions, per unit of time, was found to be a direct function of the osmolality or specific gravity of the test solutions. The greatest amount of dye was released in the shortest time from the capsules contacted with test solutions containing no NaCl, and the least amount of dye was released per unit of time from the capsules contacted with the test solution containing 4M NaCl. From the data obtained, calibration curves were prepared relating absorbance per unit of time with the known specific gravity of the respective test solution.

The foregoing method was then used to determine the specific gravity of a number of aqueous NaCl solutions, the specific gravity being arrived at by applying the absorbance measurement obtained for each solution to the appropriate calibration curve previously developed. The method was found to be sufficiently precise to resolve differences of as little as 0.050 specific gravity units between test solutions amd was also found to be useful in determining the specific gravity of such other aqueous solutions as urine.

EXAMPLE 2

This example illustrates incorporation of the microcapsules with an absorbent carrier matrix.

In this instance, an aqueous solution of sodium chloride was formed in situ by using NaOH to neutralize HCl produced by the polymer formation, and, together with the dye precursor chromotropic acid, was encapsulated within a polyamide membrane. The following charges were prepared:

| In flask; | 55 ml | mineral oil |
| | 25 ml | carbon tetrachloride |
| | 1.0 gm | bentonite |
| In 1st beaker: | 3.0 ml | H₂O |
| | 0.4 gm | NaOH |
| | 0.75 ml | ethylenediamine |
| | 0.75 ml | diethylenediamine |
| | 0.1 gm | 4,5-dihydroxynaphthalene-2,7-disulfonic acid (chromatropic acid) |
| In 2nd beaker: | 6.0 ml | carbon tetrachloride |

-continued

| | 6.0 ml | pentane |
| | 3.0 ml | sebacyl chloride |
| | 25.0 μl | trimesoyl chloride |

Using the above charges, microcapsules were prepared following the procedure described in Example 1.

The complementary dye component for the chromatropic acid, i.e., diazotized 2,4-dichloroaniline was formed in an impregnating solution prepared according to the procedure described in U.S. Pat. No. 3,585,001 by combining the following constituents in the order listed and with continuous mixing:

| Compound | Amount |
|---|---|
| Methanol | 20.0 ml |
| 2,4-dichloroaniline | 0.20 gm |
| distilled H₂O | 20.0 ml |
| sodium nitrite | 0.10 gm |
| 1,5-naphthalanedisulfonic acid, disodium salt | 0.60 gm |
| sodium lauryl sulfate | 1.50 gm |
| sulfosalicylic acid | 2.0 gm |
| methanol | 60.0 ml |

Whatman 3MM filter paper was immersed in the above solution and immediately removed. The impregnated paper was then air dried and cut into 5 mm by 5 mm square pieces. Each impregnated carrier matrix thus produced was mounted on end portion of a polystyrene sheet plastic carrier strip by the use of double-faced adhesive tape.

The microcapsules prepared as described above were incorporated with the carrier matrix containing the complementary component according to the following procedure. About 50 μl of a 2% (w/v) solution of hydroxypropyl cellulose in chloroform was applied to the impregnated matrix and the microcapsules were then uniformly sprinkled over the matrix surface. Within minutes the chloroform evaporated, thus uniformly incorporating the microcapsules on and with the impregnated matrix and the hydroxypropyl cellulose binder material to form the finished test device.

To determine the sensitivity of the test devices thus prepared, the matrix portions of finished test devices were, respectively, momentarily immersed in and withdrawn from aqueous test solutions containing NaCl concentrations of 0, 0.4 M, 0.8 M, 1.2 M and 1.6 M. In terms of specific gravity, these salt concentrations correspond to 1.000, 1.010, 1.020, 1.030 and 1.040 specific gravity units respectively. A deep red or burgundy color developed and stabilized on the matrix within about 6 minutes after the matrix was immersed in the test solution, the intensity of the color varying inversely with the concentration of NaCl in, and hence the specific gravity of, the test solution. The color was produced by reaction of chromotropic acid released from the microcapsules and the complementary dye component impregnated into the carrier matrix. By visual comparison it was possible to resolve differences in color resulting from contact with test solutions differing by only 0.01 specific gravity units. Similar results were obtained using various other aqueous saline solutions, including urine, in place of the saline test solutions described.

While, the invention as described is useful in the determination of the specific gravity of aqueous saline solutions, it will be obvious to those skilled in the art that by the use of the appropriate solvent and solute in the internal phase of the microcapsules, the invention is adapted for use in the determination of the specific gravity of a wide variety of other test solutions.

What is claimed is:

1. A device for the determination of specific gravity or osmolality of a liquid, which comprises:
    a carrier matrix incorporated with microcapsules having osmotically fragile, semipermeable polymeric membrane walls encapsulating therein a solute and a coloring substance, said capsules being capable of releasing their encapsulated contents to produce a color change upon occurrence of a preselected osmotic gradient across the capsule wall.

2. A device according to claim 1, wherein the carrier matrix is additionally incorporated with a complementary dye component when the microcapsules contain a dye precursor.

3. A device according to claim 1, wherein the microcapsules are desiccated.

4. A method for the determination of specific gravity or osmolality of a liquid, which comprises:
    contacting the test device of claim 1 with the liquid and observing any color change on the matrix as a measure of the specific gravity or osmolality of the liquid substance.

5. A method for the determination of specific gravity or osmolality of a liquid, which includes the step of contacting the liquid with a composition and observing color formation in the liquid substance as a measure of the specific gravity or osmolality of the liquid substance, wherein the composition comprises:
    microcapsules having osmotically fragile, semipermeable polymeric membrane walls encapsulating therein a solute and a coloring substance.

6. A method according to claim 5 wherein the microcapsules are desiccated.

7. Test means for determination of specific gravity or osmolality of a liquid, comprising a plurality of osmotically fragile, semipermeable membrane capsules each enclosing an inner phase of predetermined specific gravity containing a solute and a coloring substance, contact of said test means with a liquid having a specific gravity lower than said predetermined specific gravity producing hydrostatic pressure within said capsules which is effective to cause release of said inner phase from said capsules, the density of the color produced by release of the coloring substance from said capsules upon such contact being inversely related to and indicative of the specific gravity of the liquid contacted.

* * * * *